United States Patent [19]

Jarrousse et al.

[11] Patent Number: 5,891,426

[45] Date of Patent: Apr. 6, 1999

[54] SCREENING OF CANDIDATES FOR BIOLOGICAL HAIR CARE ACTIVITY

[75] Inventors: Françoise Jarrousse, Livry Gargan; Stéphane Commo; Olivier Gaillard, both of Paris; Bruno Bernard, Neuilly Sur Seine, all of France

[73] Assignee: Societe L'Oreal S.A., Paris, France

[21] Appl. No.: 800,457

[22] Filed: Feb. 18, 1997

[30] Foreign Application Priority Data

Dec. 15, 1996 [FR] France ................................. 96 01885

[51] Int. Cl.⁶ ........................................................ A61K 7/06
[52] U.S. Cl. ..................... 424/70.1; 424/94.1; 424/94.67; 424/543; 514/880; 435/1; 435/70.1; 435/240.2; 435/240.21; 435/240.22
[58] Field of Search ................................. 424/70.1, 94.1, 424/94.67, 543; 514/880; 435/1, 70.1, 240.2, 240.21, 240.22

[56] References Cited

U.S. PATENT DOCUMENTS 5,667,961  9/1997  Bernard et al. ............................. 435/1

FOREIGN PATENT DOCUMENTS 0434319  6/1991  European Pat. Off. .

OTHER PUBLICATIONS

Journal of Ivestigative Dermatology, vol. 105, No. 2, Aug. 1995, New York, N.Y., pp. 177–183, XP000196475 Scandurro et al: "Immortalized rat whisker dermal papilla cells cooperate with mouse immature hair follicle buds to activate type IV procollagenases in collagen matrix coculture: Correlation with ability to promote hair follicle development in nude mouse grafts."

Journal of Investigative Dermatology, vol. 101, No. 1 (Supplement), Jul. 1993, New York, N.Y., pp. 27S–32S, XP000196474 Yuspa et al: "Regulation of hair follicle development: an in vitro model for hair follicle invasion of dermis and associated connective tissue remodeling."

SIGMA chemical company catalog, p. 275 (showing different types of collagenases), 1992.

Primary Examiner—Thurman K. Page
Assistant Examiner—Lakshmi Channavajjala
Attorney, Agent, or Firm—Burns, Doane, Swecker & Mathis, L.L.P.

[57] ABSTRACT

The invention concerns a procedure for testing a potentially-active substance used in the hair-care field, this procedure being characterized by the fact that a fragment of at least one hair follicle without dermal papilla is isolated, this fragment being taken from beneath the point of attachment of the sebaceous gland and excluding the portion of the hair shaft located above the point of attachment of the sebaceous gland; that this fragment is incubated in a suitable culture medium for a sufficient period; that this fragment is placed in contact with a potentially-active hair-care substance; that a marker of the activity of said tested substance is quantitatively determined; and that the results of this determination are assessed as they compare to a control.

23 Claims, No Drawings

SCREENING OF CANDIDATES FOR BIOLOGICAL HAIR CARE ACTIVITY

BACKGROUND OF THE INVENTION

1. Technical Field of the Invention

The present invention concerns a procedure for testing a potentially-active substance used in the hair-care field.

The term "hair-care field" encompasses everything related to the hair of an individual.

Accordingly, the expression "potentially active substance used in the hair-care field," or, in the remainder of the text, the term "substance" signifies any molecule or set of molecules producing potential activity in the hair-care field and, in particular, any molecule or set of molecules potentially producing an effect on the survival, slowing or stoppage of growth, loss by falling, or aggravated growth of the hair follicles. The substance to be tested can be used according to the invention procedure either in molecular form or as a composition containing the molecule to be tested.

2. Description of the Prior Art

At present, prior art cites two principal methods for testing a potentially-active substance in the hair-care field.

The first consists in performing trials on volunteers and in noting relatively rapidly the effects produced by the tested substance. This method obviously presents many disadvantages, including, in particular, that of dealing with humans, thereby obviously restricting the scope of application of this method for ethical reasons. As a result, the number and quality of the substances tested is limited. Furthermore, these tests require burdensome implementation procedures and are conducted over long periods of time. In most cases, the test results entail observations of phenotypical modifications of the hair follicles The second method known according to prior art is described in Patent No. EP-434,319. It includes dissection of the hair follicle and involves taking a skin sample containing follicles, cutting the hair shaft beneath the dermal/epidermal junction, then in isolating the follicle from the surrounding skin without damaging the bulb. One modification of this method as suggested by Williams and Stenn (*Dev. Biol.*, 165, 469–479 (1994)) consists in preliminarily cutting the biopsy into thin vertical slices 1 mm thick, then in performing the dissection according to the technique described in Patent No. EP-434,319, by pulling the follicle from its environment using tweezers.

This second method and the variant thereof require the preservation of all of the characteristics making the hair follicle viable, that is, those characteristics capable of regenerating a hair shaft in vitro (on this subject, see *Science des traitements capillaires*, Charles Zviak, Masson, 1987, in which these characteristics are described). Accordingly, the follicle must be preserved, most notably along with its bulb and dermal papilla. This can be achieved only by meticulous dissection, a process which makes implementation of the procedure burdensome. It will be easily understood that, in terms of usable, viable hair follicles, the yield from such dissection is extremely small.

The Applicant thus sought a new procedure for testing a potentially-active substance used in the hair-care field and which preserves the efficacy of conventional methods while facilitating implementation of the procedure.

SUMMARY OF THE INVENTION

The Applicant discovered that, in order to test a potentially-active hair-care substance, it was possible to use a fragment of at least one hair follicle without dermal papilla and located beneath the point of attachment of the sebaceous gland, but excluding the portion of the hair shaft located above the point of attachment of the sebaceous gland.

This discovery serves as the basis for this invention. One of the many advantages deriving from the invention is that, henceforth, it will no longer be necessary to dissect the hair follicle with extreme caution, since, in the test according to the invention, the hair follicle may not be viable in the sense explained above; that is, it may not be capable of regenerating a hair shaft in vitro.

This facilitates significantly the job of-the person who must prepare the components needed to conduct the test and increases significantly the number of usable follicles contained in the skin sample containing follicles.

Accordingly, the invention concerns a procedure for testing a potentially active hair-care substance and is characterized by the fact the following steps are carried out:

(i) a fragment of least one hair follicle without dermal papilla is isolated beneath the point of attachment of the sebaceous gland, while excluding the portion of the hair shaft located above the point of attachment of the sebaceous gland, (ii) this fragment is incubated in a suitable culture medium, (iii) this fragment is placed in contact with a potentially active hair-care substance for a sufficient period, (iv) the marker of the activity of this tested substance is quantitatively determined and the analysis results are assessed in comparison with a control.

DETAILED DESCRIPTION OF BEST MODE AND SPECIFIC/PREFERRED EMBODIMENTS OF THE INVENTION

In the remainder of the text, the term "fragment" should be understood to mean a "fragment of at least one hair follicle without dermal papilla located beneath the point of attachment of the sebaceous gland, but excluding the portion of the hair shaft located above the point of attachment of the sebaceous gland."

The follicle fragment that can be used according to the invention may be taken from a hair follicle isolated using any dissection method known to those skilled in the art.

Dissection may be performed using known conventional methods, such as the technique described in "Cultivation of Murine Hair Follicles as Organoids in a Collagen Matrix," in *Journal of Investigative Dermatology*, 89, No. 4 (1987), pp. 369–379, in which the follicle is isolated by causing collagenase to digest the dermis; or the technique described in Patent No. 434,319 (cited above); or again, the technique described in the article by Williams and Stenn (also mentioned above); or finally, the method described by the Applicant in its patent application filed in France under No. 95-08465, which consists in removing, in an intact skin sample, the papilla and bulb of hair follicles from their dermal environment, while keeping intact the epidermal environment. These three last-mentioned techniques use only mechanical means. In accordance with the invention, use is preferably made of the technique described by applicant in the patent application filed in France under No. 95-08465.

As stated in the invention, it is not necessary that the hair follicle be viable. Proper conduct of the procedure does not dictate that the fragment exhibit properties conferring viability, which are, however, essential to implementation of conventional procedures disclosed in prior art. Thus, the fragment need not incorporate all of the parts which, according to the specialist, compose it (*Science des traitements capillaires*, Charles Zviak, Masson, 1987).

As a result, any other known dissection technique not necessarily isolating a viable hair follicle can be used to prepare the hair follicle.

Thus, the bulb may not be included in the hair follicle fragment usable according to the invention. According to a preferred embodiment of the invention, the hair follicle fragment used has no bulb.

In humans, the growth and regeneration of hair are determined principally by the activity of the hair follicles. They function cyclically, and this cyclic activity includes three main phases, i.e., the anagen, catagen, and telogen phases. The active growth phase or anagen, which lasts for several years during which the hairs become longer, is followed by the very short, temporary catagen phase, then by the so-called telogen, or resting, phase, which lasts for several months. At the end of the resting phase, the hairs fall out and another cycle begins. Thus, hair regenerates itself continuously, and, out of the approximately 150,000 hairs on the scalp at any one time, about 10% are at rest and will be replaced within several months. Obviously, the test as specified by this invention may be conducted using a fragment taken from any hair follicle, whatever the phase of the hair cycle which that fragment is undergoing at the time the sample is taken.

Preferably, the fragment used in the invention procedure is a fragment taken from a hair follicle in the anagen phase.

Thus, the fragment used according to the invention is characterized by the presence of at least one of the following specific morphological features:

(i) thickening of the basal membrane into not actually applied).
a refringent eosinophilic, so-called hyaline, layer located at the interface between the outer sheath of the hair follicle and the connective sheath;

(ii) program for specific differentiation of the keratinocytes in the outer sheath, which differs from that of the keratinocytes in the upper part of the hair follicle or from those of the epidermis;

(iii) absence of an antigen recognized by a desmoglein-fighting antibody in the outer sheath;

(iv) presence in the outer sheath of a baso-lateral distribution of the integrins $\alpha 2\beta 1$ and $\alpha 3\beta 1$ in the basal keratinocyte layer;

(v) presence of the receptor of the epidermal growth factor (EGF) on the surface of the basal keratinocytes and of the suprabasal keratinocytes in the outer sheath.

The fragment used according to the invention will preferably incorporate all of the specific morphological features described above.

After the fragment is isolated, it is placed in a suitable culture medium. This nutritive medium is composed of at least those constituents necessary for survival of the fragment. It may obviously contain any other constituent necessary, for example, for the growth of the hair follicle, such as insulin, glutamine, and hydrocortisone.

As examples of culture mediums well known to the specialist, mention may be made of the modified Dulbecco MEM medium, the Williams E medium, the F12 medium, the HAM medium, and the RPMI1640 medium, which are sold by the Gibco-BRL, Biomed, Boehringer, and Sigma companies.

The Williams E medium is preferred.

In general, the contact time of the hair follicle fragment and the potentially active hair-care substance to be tested depends on the time needed for the fragment to respond to said substance; that is, the time needed to see a modification of the level of expression of the marker of the activity of the substance tested. The marker is then quantitatively determined.

This incubation time may range from several seconds to several days. As an indication, the incubation normally ranges between 10 seconds and 120 hours, and preferably between 1 and 72 hours.

The term "marker of the activity of the potentially active hair-care substance tested" signifies, in accordance with the invention, any element whose presence, absence, modification of expression or modification of distribution can be measured as a response to the contact between the hair follicle fragment and said substance to be tested. Non-limiting examples of markers include nucleic acids (ribonucleic or deoxyribonucleic acid), proteins or linked or non-linked protein groups, ions, cellular organelles, lipids, and polyosides.

The activity of the substance to be tested is thus shown by variations in the marker of the activity of the substance tested that has been selected for quantitative determination. "Variation" means any modification of the quantity, concentration, or distribution of the marker subjected to quantitative analysis.

To this end, the procedure according to the invention includes a step entailing the quantitative determination of the marker of the activity of the substance tested.

Following incubation, this analysis may be carried out directly on the culture medium for elements excreted by the fragment, or in the hair follicle fragment for unexcreted elements. Thus, and more especially in the case in which the element sought for is not excreted, an additional step may be performed before analysis, during which the hair follicle fragment is ground in order to provide greater access to the marker of the activity produced by the tested substance to be quantitatively analyzed.

Obviously, regardless of the mode of implementation of the procedure according to the invention, any analytic technique known to the specialist may be used. As non-limiting examples, mention may be made of methods used to quantitatively determine proteins or nucleic acids by means of colorimetry, electrophoresis, reverse transcriptase and amplification using the chain polymerization technique, mass spectrography, gas or plate chromatography, immunological methods, or optical or electron microscopy to measure the quantity of an organelle.

The analytic result, which gives the variation in the marker of the activity of the tested substance selected for quantitative analysis, cannot be used directly by itself. It become useful only when compared to the result of the same analysis carried out under the same conditions, but in the absence of any contact between the hair follicle and the substance to be tested. Thus, the invention procedure includes a step during which the quantitative analysis results are assessed and compared to a control. The specialist will easily, out of habit, determine the type of control required when performing the procedure.

The applicant also found that the fragment preferably used in the invention, that is, the hair follicle fragment in the anagen phase exhibiting all of the morphological features described in the text, possesses an entirely specific biological particularity. When incubated in a suitable culture medium for sufficient time, this fragment secretes, among the collagenases, only type IV 72-kilodalton collagenase (also known by the name gelatinase A or MPP2).

However, when this fragment is incubated in the presence of a growth factor, for example the epidermal growth factor (EGF) or the tumoral type α growth factor (TGFα), synthesis of type IV 92-kilodalton collagenase (known also as gelatinase B or MPP 9) is brought about. This synthesis is inhibited when the culture medium also contains 2,4-diamino-6-piperidinopyrimidine-3-oxide, or Minoxidil, as described in U.S. Pat. No. 4,596,812.

This compound is well known to the specialist because of its effects on the growth and/or regrowth of hair.

The applicant thus suggests the use of this property of the fragment in order to assess the activity of a hair-care substance.

Accordingly, according to a special embodiment of the invention, the procedure for testing a potentially active hair-care substance is characterized by the fact that the following steps are performed:

(i) a fragment of at least one hair follicle without dermal papilla is isolated, this fragment being found beneath the point of attachment of the sebaceous gland and excluding the portion of the hair shaft located above the point of attachment of the sebaceous gland, (ii) this hair follicle is incubated in a suitable culture medium in the presence of the epidermal growth factor (EGF) or type α tumoral growth factor (TGFα) for a sufficient period of time (T1), (iii) this hair follicle is placed in contact with a potentially active hair-care substance for a sufficient period of time, (iv) the type IV 92-kilodalton collagenase is quantitatively determined and the analysis results are assessed in comparison to a control.

In conformity with the invention, the growth factor is used at a concentration of between 0.001 ng/ml and 100 ng/ml, and preferably between 0.1 ng/ml and 10 ng/ml.

The growth factor used is preferably the epidermal growth factor (EGF).

The suitable culture medium employed in accordance with the invention is identical to that described in the text.

With respect to the invention, the incubation time (T I) of the hair follicle and the epidermal growth factor (EGF) or the type α tumoral growth factor (TGFα) is between 5 seconds and 45 days, and preferably between 1 hour and 72 hours.

Without repeating the list given elsewhere, it is obvious that any analytic method known to those skilled in the art may be employed to assess the degree of expression of the type IV 92-kilodalton collagenase. As examples, mention may be made of the determination of protein content using any conventional technique, or estimation of the quantity of messenger ribonucleic acid of the type IV 92-kilodalton collagenase.

The control in comparison to which the analysis results are assessed in accordance with the invention consists, quite obviously, in the level of expression of the type IV 92-kilodalton collagenase under the same experimental conditions, but in the absence of any contact between the hair follicle and the substance to be tested.

The potentially-active hair-care substances to be quantitatively determined normally relate to a modification of the condition of the hair of the subject, and preferably the present or future condition thereof.

In general, the substances submitted for testing produce an effect either on the density of the hair follicles or on the quality or quantity of these follicles. These substances may potentially produce an effect, for example, on the slowing or stoppage of growth, the loss by failing, or the aggravated growth of the hair follicles.

Accordingly, the invention allows testing of potentially-active hair-care substances affecting slowing or stoppage of growth, loss by falling, or the aggravated growth of hair follicles.

If the slowing or stoppage of growing or the loss of hair follicles by falling only is considered, the ultimate consequence for the subject is relatively marked alopecia, which, it is known, may have esthetic, psychological, and/or social consequences for the affected subject.

More especially, the procedure according to the invention allows the testing of substances which may have an effect on the slowing or stoppage of growth or the loss of hair follicles.

The invention procedure thus makes it possible to test potentially-active hair-care substances used in the treatment of alopecia.

The term "alopecia" covers a wide range of attacks on the hair follicle, which, whatever the cause, entail the definitive, partial, or generalized loss of hair. Such conditions include, for example, androgenetic alopecia, alopecia areata (pelade), alopecia totalis, or alopecia universalism The invention also relates to the use of a fragment as specified above in a procedure for testing a potentially-active hair-care substance.

Specifically, the invention concerns the use of a fragment as specified above in a procedure for testing a potentially-active substance used for the growth and/or regrowth of the hair follicle, and more particularly, for the treatment of alopecia.

One of the advantages of the invention lies in the fact that it yields a simple procedure for assessing the activity of a potentially-active hair-care substance, especially on the growth and/or regrowth of the hair follicle and, more especially, in the treatment of alopecia. The substance tested in this way could subsequently be used in the preparation of a cosmetic composition or drug intended for the treatment of hair disorders, especially those linked to the growth and/or regrowth of the hair follicle, and, more particularly, those intended for the treatment of alopecia.

Illustrative examples which do not in any way restrict the scope of the invention will now be given.

EXAMPLE 1

Measurement of the Effect of Minoxidil on 72 kD Collacenase and on 92 kD Collapenase in the Presence of Epidermal Growth Factor:

150 fragments of hair follicles without dermal papillae located beneath the point of attachment of the sebaceous gland and excluding the portion of the hair shaft located above the point of attachment of the sebaceous gland were prepared, using the technique described by the Applicant in its patent application filed in France under No. 95-08465, from dissected hair follicles taken from a skin sample obtained from a plastic facial operation. A scalpel was used to isolate a fairly thin strip on the skin sample. The adipose tissue surrounding the hair follicles was removed with micro tweezers. Under a microscope, the follicle fragments were then cut using a scalpel.

The fragments were then incubated in Williams E medium, to which were added penicillin and streptomycin in a final concentration of 50 Ul/ml, glutamine in a 2 mM concentration, cow insulin in a concentration of 0.01 mg/ml, and hydrocortisone in a concentration of 0.04 μg/ml, in the wells of 24-well Costar dishes, 1 fragment per well. Each well contained 1 ml of medium.

Four series were thus produced:

A: Control series: 6 fragments in Williams E medium.

B: 6 fragments in Williams E medium supplemented with epidermal growth factor (EGF) in a final concentration of 10 ng/ml.

C: 6 fragments in Williams E medium to which Minoxidil in a final concentration of 1 mM was added.

D: 6 fragments in Williams E medium to which were added epidermal growth factor (EGF) in a final concentration of 10 ng/ml and Minoxidil in a final concentration of 1 mM.

The four series were incubated at 37° C.

On a daily basis, 0.5 ml of the medium was collected and quantitatively analyzed for collagenolytic activity using the zymography technique (Huessen, C. and Dowdle, E. B., *Analytical Biochemistry* (1980), 102, pp. 196–202).

The proteins collected in the medium were separated out according to molecular weight using conventional electrophoresis on polyacrylamide gel in a denaturing medium containing sodium dodecylsulfate (SDS) (PAGE-SDS technique). The separation gel was a 10% acrylamide gel containing gelatin in a concentration of 0.5 mg/ml. The concentration gel was a 4% acrylamide gel.

Before deposition, the proteins in each sample to be analyzed were quantitatively determined using a Biorad CD protein kit in accordance with the manufacturer's specifications.

For each sample submitted for analysis, $10\mu$ of the proteins were deposited on the electrophoresis gel. Electrophoresis was carried out at a temperature of 4° C. overnight at constant amperage of 10 mA in a Lagon system made by the Bioblock Company.

After stopping electrophoresis and unmolding, the gels were washed in distilled water containing 2.5% Triton ×100. Two 30-minute washing operations were carried out to remove all of the SDS and restore enzyme activity. The gels were then placed in an incubator at 37° C. for 24 hours in a solution containing TRIS HCl (ph=7.5, concentration=5 mM), 4% SDS, calcium chloride in a concentration of 5 mM, and 0.02% Brij 35. They were then stained with Coomassie brilliant blue for ½ hour, then decolorized for one hour.

The presence of active proteins was revealed by the appearance of clear bands on a blue background, which signaled collagenase digestion of the gelatin contained in the gel.

Results

+: marks the appearance of a band of type IV 72-kilodalton collagenase or of type IV 92-kilodalton collagenase.

−: indicates the absence of band of this type.

|   | Type IV 72-kilodalton collagenase | Type IV 92-kilodalton collagenase |
|---|---|---|
| A | + | − |
| B | + | + |
| C | + | − |
| D | + | − |

Synthesis of the type IV 92-kilodalton collagenase occurred in the hair follicle fragment incubated in the presence of EGF. Minoxidil inhibited this synthesis.

What is claimed is:

1. A method for testing whether a substance is suitable for use as a hair-care substance comprising the following steps:

(i) isolating a fragment of at least one hair follicle which does not comprise dermal papilla by removing such hair follicle beneath the point of attachment of the sebaceous gland, while excluding the portion of the hair shaft located above the point of attachment of the sebaceous gland;

(ii) placing the resulting hair follicle fragment in a suitable culture medium;

(iii) incubating said hair follicle fragment with a substance which is to be screened for its ability to be used as a hair-care substance for a sufficient time to determine whether said substance affects expression of a marker substance wherein the said marker substance is type IV 72-kilodalton collagenase or type IV 92-kilodalton collagenase; and (iv) determining whether such substance is a suitable hair-care substance by quantifying the expression of said marker substance and comparing said value to marker substance expression by a control hair follicle fragment treated under identical conditions, except that it is not placed in contact with said substance which is being screened for its ability to unction as a suitable hair-care substance.

2. The method according to claim 1, wherein said marker substance is a substance the amount of which correlates to slowing or stopping of hair growth, hair loss, or the aggravated growth of hair follicles.

3. The method according to claim 1, wherein said hair follicle is isolated by dissection.

4. The method according to claim 1, wherein said follicle fragment exhibits at least one of the following morphological characteristics:

(i) thickening of the basal membrane into a refringent eosinophilic layer which is located at the interface between the outer sheath of said hair follicle fragment and the connective sheath;

(ii) a pattern of specific differentiation of the keratinocytes in the outer sheath, which differs from that of the keratinocytes in the upper part of the hair follicle, and from those comprised in the epidermis;

(iii) lacks an antigen in the outer sheath which is recognized by an anti-desmoglein antibody;

(iv) comprises in the outer sheath a basal lateral distribution of the integrins $\alpha 2\beta 1$ and $\alpha 3\beta 1$ in the basal keratinocyte layer; and (v) comprises an epidermal growth factor (EGF) receptor comprised on the surface of the basal keratinocytes and the suprabasal keratinocytes comprised in the outer sheath.

5. The method according to claim 4, wherein said hair follicle fragment exhibits all of said morphological features (I)–(V).

6. The method according to claim 1, wherein said hair follicle is in the anagen plase.

7. The method according to claim 1, wherein said culture medium is selected from the group consisting of Dulbecco MEM medium, Williams E medium, F12 medium, HAM medium, and RPMI1640 medium.

8. The method according to claim 7, wherein said culture medium is Williams E medium.

9. The method according to claim 1, wherein said hair follicle fragment is incubated for a time ranging between 10 seconds and 120 hours.

10. The method according to claim 9, wherein said incubation time ranges between 1 and 72 hours.

11. The method according to claim 1, wherein said marker which is quantified to assess the ability of said substance to function as a suitable hair-care substance is selected from the group consisting of a nucleic acid, a protein, a group of proteins, an ion, a cell organelle, a lipid, and a polyoside.

12. The method according to claim 1, wherein said marker which is quantified to assess the ability of said substance to function as a hair-care substance is quantified directly in the culture medium.

13. The method according to claim 1, wherein said marker, the expression of which is quantified to determine the ability of said screened substance to function as a hair-care substance, is measured in the cultured hair follicle fragment.

14. The method according to claim 13, wherein prior to quantitating the amount of said marker, the hair follicle fragment is ground.

15. A method for testing the ability of a particular substance to function as a suitable hair-care substance which comprises the following steps:
  (i) isolating a fragment of at least one hair follicle which does not comprise dermal papilla by removing said hair follicle at a point below the point of attachment of the sebaceous gland and excluding the portion of the hair shaft located above the point of attachment of the sebaceous gland;
  (ii) incubating said hair follicle fragment in a suitable culture medium in the presence of epidermal growth factor (EGF) or type α tumorous growth factor (TGFα) for a period of time (T1);
  (iii) placing said incubated hair follicle fragment in contact with a potentially active hair-care substance for a sufficient period of time to determine whether said potentially active hair-care substance has an effect on the expression of type IV 92-kilodalton collagenase; and
  (iv) quantitatively determining the amount of type IV 92-kilodalton collagenase and comparing the amount thereof to a control hair follicle fragment which is treated under identical conditions, except that said hair follicle fragment is not placed in contact with said potentially active hair-care substance.

16. The method according to claim 15, wherein said growth factor is contained in a concentration ranging from between 0.001 ng/ml and 100 ng/ml.

17. The method according to claim 16, wherein the concentration of said growth factor ranges between 0.01 ng/ml and 10 ng/ml.

18. The method according to claim 15, wherein said growth factor is epidermal growth factor (EGF).

19. The method according to claim 15, wherein said incubation time (T1) ranges between 5 seconds and 45 days.

20. The method according to claim 15, wherein said incubation time (T1) ranges between 1 hour and 72 hours.

21. The method according to claim 1, wherein said substance is screened for its ability to affect one of the following hair growth properties:
  (i) effect on slowing or retarding the growth of hair;
  (ii) affecting the loss of hair; and
  (iii) affecting the aggravated growth of hair follicles.

22. The method according to claim 1, wherein the ability of the substance to retard or prevent the growth and loss of hair follicles is determined.

23. The method according to claim 1, wherein said substance is screened for its ability to treat alopecia.

* * * * *